(12) United States Patent
Gwon et al.

(10) Patent No.: US 9,310,387 B2
(45) Date of Patent: Apr. 12, 2016

(54) TEST APPARATUS AND METHOD OF CONTROLLING THE SAME

(71) Applicant: SAMSUNG ELECTRONICS CO., LTD., Suwon-si (KR)

(72) Inventors: Se Do Gwon, Goyang-si (KR); Kyu Tae Kang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/251,111

(22) Filed: Apr. 11, 2014

(65) Prior Publication Data

US 2015/0031136 A1    Jan. 29, 2015

(30) Foreign Application Priority Data

Jul. 24, 2013    (KR) .................... 10-2013-0087515

(51) Int. Cl.
| | | |
|---|---|---|
| *G01N 35/00* | (2006.01) | |
| *G01N 21/84* | (2006.01) | |
| *G01N 21/00* | (2006.01) | |
| *G05D 3/12* | (2006.01) | |
| *G05D 3/00* | (2006.01) | |

(52) U.S. Cl.
CPC ........ *G01N 35/00584* (2013.01); *G01N 21/8483* (2013.01); *G05D 3/125* (2013.01); *Y10T 436/115831* (2015.01); *Y10T 436/12* (2015.01)

(58) Field of Classification Search
CPC ............. Y10T 436/00; Y10T 436/12; G01N 35/00584; G01N 35/00; G01N 21/8483; G01N 21/84; G01N 21/00; G05D 3/125; G05D 3/12; G05D 3/00

USPC ................. 436/50, 43; 422/68.1, 50
See application file for complete search history.

(56) References Cited

U.S. PATENT DOCUMENTS

| | | |
|---|---|---|
| 5,654,803 A | 8/1997 | Howard, III et al. |
| 6,024,920 A | 2/2000 | Cunanan |
| 6,071,477 A | 6/2000 | Auclair et al. |
| 2011/0017905 A1 | 1/2011 | Yeo |
| 2013/0143327 A1 | 6/2013 | Kim et al. |

(Continued)

FOREIGN PATENT DOCUMENTS

| | | |
|---|---|---|
| DE | 4013588 A1 | 11/1991 |
| DE | 4117008 A1 | 11/1991 |
| EP | 0245920 A2 | 11/1987 |

(Continued)

OTHER PUBLICATIONS

Communication issued Feb. 27, 2015, by the European Patent Office in related Application No. 14168099.1.

*Primary Examiner* — Christine T Mui
(74) *Attorney, Agent, or Firm* — Sughrue Mion, PLLC (57) ABSTRACT

A test apparatus, which may compare detection data of a detector with reference data and correct a positional error in the detector due to the failing of a motor, and a method of controlling the same are provided. The test apparatus includes a detector configured to irradiate light to a plurality of chambers of a reaction device and detect a detection target, a motor configured to move the detector such that light is irradiated to the plurality of chambers, and a controller configured to compare detection data of the detector regarding the reaction device with reference data, determine a positional error in the detector, and correct the positional error.

20 Claims, 11 Drawing Sheets

(56) References Cited

U.S. PATENT DOCUMENTS

2013/0196360 A1* 8/2013 Yeo et al. .................. 435/28
2013/0212749 A1* 8/2013 Watanabe ............... G21K 7/00
850/4

FOREIGN PATENT DOCUMENTS

| GB | 1485506 | | 9/1977 | |
|----|---------|---|--------|---|
| KR | 10-2012-0007650 | * | 1/2012 | ............. G01N 33/53 |

* cited by examiner

TEST APPARATUS AND METHOD OF CONTROLLING THE SAME

CROSS-REFERENCE TO RELATED APPLICATION

This application claims priority from Korean Patent Application No. 10-2013-0087515, filed on Jul. 24, 2013 in the Korean Intellectual Property Office, the disclosure of which is incorporated herein by reference.

BACKGROUND

1. Field

Apparatuses and methods consistent with exemplary embodiments relate to a test apparatus configured to measure a specimen contained in a biochemical sample.

2. Description of the Related Art

An apparatus for and method of analyzing fluidic samples are required in various fields, such as environmental monitoring, food inspection, and medical diagnosis. In recent years, a downscaled, automated apparatus capable of rapidly analyzing fluidic samples has been developed.

To detect a test material contained in a fluidic sample, a reaction between the test material and a specific material may be used. Also, optical data regarding the fluidic sample may be measured using an optical sensor, and the concentration of the test material may be determined based on the magnitude of the measured optical data and/or a variation in the magnitude of the measured optical data.

When a motor configured to move the optical sensor during analysis fails, any detected results may be unreliable as a result thereof. Thus, it is necessary to correct for errors due to the failing of the motor and improve the reliability of the detection results.

SUMMARY

Exemplary embodiments provide a test apparatus, which may be configured to compare detection data of a detector with reference data and correct a positional error in the detector due to the failing of a motor, and a method of controlling the same.

In accordance with an aspect of an exemplary embodiment, there is provided a test apparatus including: a detector configured to irradiate light to a plurality of chambers of a reaction device and detect a detection target, a motor configured to move the detector such that light is irradiated to the plurality of chambers, and a controller configured to compare detection data received from the detector regarding the reaction device with reference data, determine a positional error in the detector, and correct the positional error.

The test apparatus may further include a support configured to support the reaction device inserted into the test apparatus, the support including two holes, each formed adjacent to and surrounding the reaction device, and at least one positional sensor disposed adjacent to the two holes and under the support, and configured to sense the detector when the detector moves to a position corresponding to one of the holes.

The controller may be configured to compare the detection data of the detector regarding at least one of the two holes with reference data regarding the corresponding hole, determine an extent by which the detection data of the detector is shifted from the reference data, and determine the positional error in the detector based on the extent of the shifted data.

The controller may be configured to shift the detection data regarding the plurality of chambers back by as much as the determined positional error, and correct the detection data.

The controller may be configured to drive the motor and move the detector back by as much as the positional error, thereby correcting the positional error in the detector.

The controller may be configured to compare the detection data of the detector regarding any one of the plurality of chambers of the reaction device with reference data corresponding to the detection data, determine an extent by which the detection data of the detector is shifted from the reference data, and determine the positional error in the detector based on the extent of the shifted data.

The controller may be configured to compare the detection data of the detector with the reference data, determine the positional error in the detector, and correct the positional error while the detector is moving.

The controller may be configured to drive the motor, move the detector in a first direction, and control the detector so that the detector irradiates light to each of the plurality of chambers of the reaction device and detects a detection target while moving. The controller may be configured to compare detection data of the detector regarding at least one of the two holes with reference data regarding the corresponding hole, determine an extent by which the detection data of the detector is shifted from the reference data, and determine the positional error in the detector based on the extent of the shifted data after the detector moves a predetermined distance.

The controller may be configured to compare the detection data of the detector with reference data, determine the positional error in the detector, and correct the positional error in the detector when the detector is sensed by the at least one positional sensor.

In accordance with an aspect of another exemplary embodiment, there is provided a method of controlling a test apparatus is provided, the method including: driving a motor configured to move a detector, thereby moving the detector in a first direction, comparing detection data regarding a plurality of chambers of a reaction device while the detector is in motion, with reference data and determining a positional error in the detector, and correcting the positional error.

The method may further include comparing detection data of the detector regarding any one of the plurality of chambers of the reaction device with reference data corresponding to the detection data, and determining an extent by which the detection data of the detector is shifted from the reference data, and determining the positional error in the detector based on the determined extent of shift.

The correction of the positional error may include shifting the detection data of the detector back by as much as the determined positional error and correcting the detection data.

The correction of the positional error may include driving the motor, thereby moving the detector by as much as the positional error to correct the positional error in the detector.

The test apparatus may include a support configured to support the reaction device inserted therein, the support including two holes each formed adjacent to and surrounding a position in which the reaction device is located, and at least one positional sensor disposed adjacent to and under the support and configured to sense the detector when the detector moves to a position corresponding to one of the holes.

The determination of the positional error may include comparing the detection data of the detector regarding at least one of the two holes with reference data regarding the corresponding hole, determining an extent by which the detection data of the detector is shifted from the reference data, and determining the positional error in the detector based on the extent of shift.

The method may further include controlling the detector so that the detector irradiates light to each of the plurality of chambers of the reaction device and detects a detection target while moving, comparing detection data of the detector regarding at least one of the two holes with reference data regarding the corresponding hole and determining an extent by which the detection data of the detector is shifted from the reference data when the detector moves a predetermined distance, and determining the positional error in the detector based on the determined extent of shift.

The method may further include controlling the detector so that the detector irradiates light to each of the plurality of chambers of the reaction device and detects a detection target while moving, comparing detection data of the detector regarding at least one of the two holes with reference data regarding the corresponding hole and determining an extent by which the detection data of the detector is shifted from the reference data when a positional sensor located in the moving direction senses the detector, and determining the positional error in the detector based on the determined extent of shift.

In accordance with an exemplary embodiment, positional errors in a detector and data due to the failing of a motor can be corrected without additional mechanical hardware or circuitry.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Reference will now be made in detail to exemplary embodiments, examples of which are illustrated in the accompanying drawings, wherein like reference numerals refer to like elements throughout.

Figure 1:
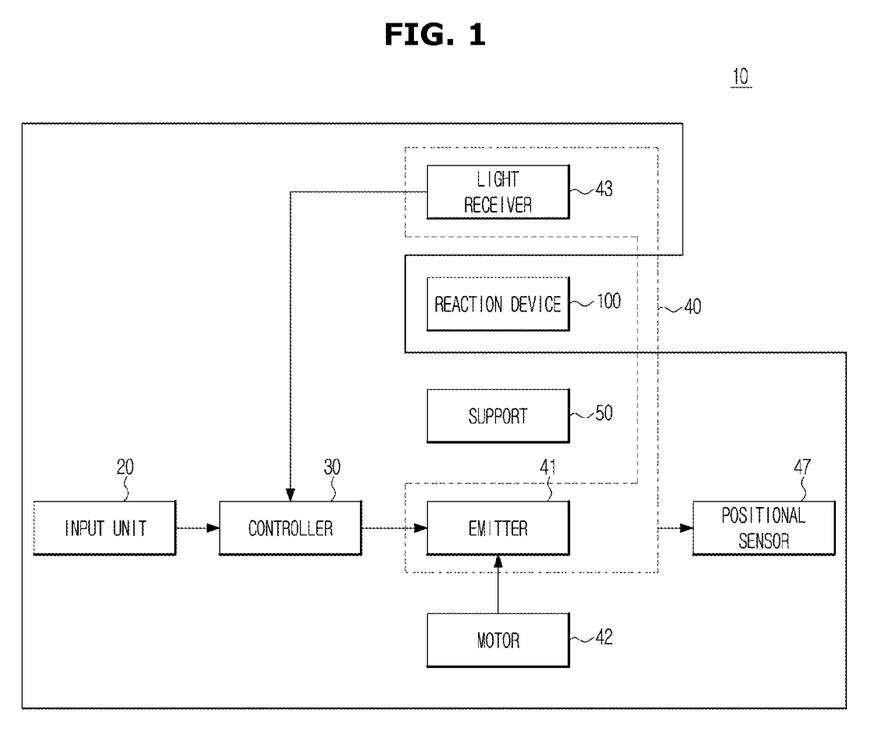
FIG. 1 is a block diagram illustrating the configuration of a test apparatus in accordance with an exemplary embodiment.

FIG. 1 is a block diagram showing construction of a test apparatus 10 in accordance with an exemplary embodiment. Referring to FIG. 1, the test apparatus 10 may include an input unit 20 through which a user instructions are input, a detector 40 including an emitter 41 configured to radiate light onto a reaction device 100 and a light receiver 43 configured to detect light, which is transmitted through a sample or reflected by the sample, a motor 42 configured to provide power required to move the detector 40, a support 50 configured to support a test device 120 of the reaction device 100 when the reaction device 100 is inserted into the test apparatus 10, a positional sensor 47 configured to sense a position of the detector 40, and a controller 30 configured to control general operations and functions of the test apparatus 10 in response to a command input via the input unit 20 and correct any positional errors in the detector 40 due to the failing of the motor 42.

The reaction device 100 may be a device in which a biochemical sample (e.g., blood) is contained and in which a biochemical reaction can be performed to determine whether or not a specimen is contained in the sample and/or to calculate the concentration of the specimen. In various embodiments, the reaction device 100 may contain a reagent configured to react with and/or detect the specimen.

The reaction device 100 may include a microfluidic device or a fluid analysis cartridge configured to move a fluid using centrifugal force or capillary attraction as a driving pressure. Hereinafter, the fluid analysis cartridge will be described as an example of the reaction device 100.

Figure 2:
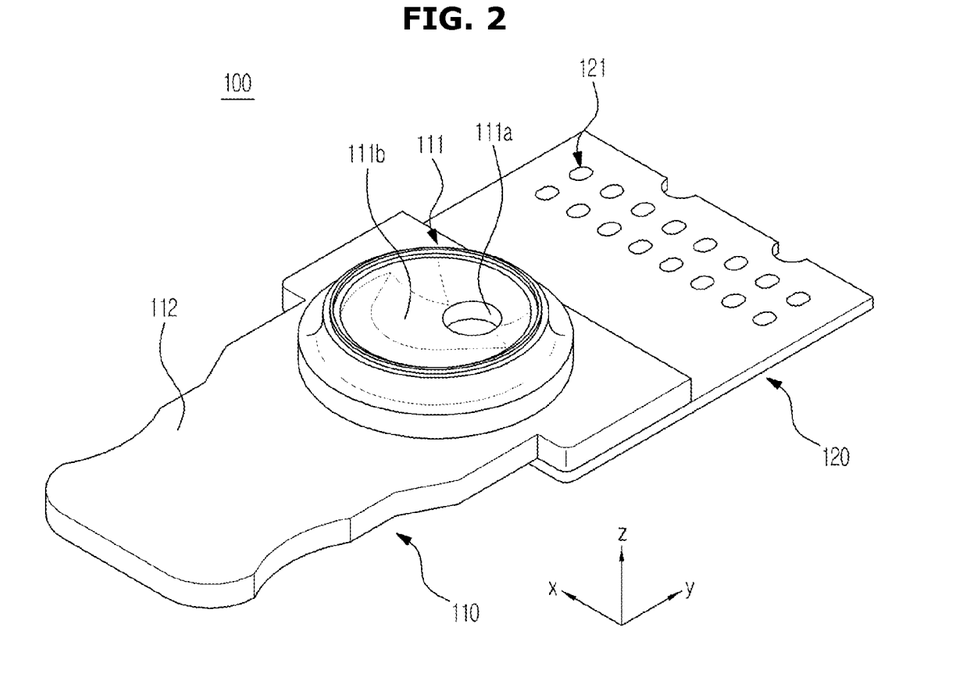
FIG. 2 is a perspective view of a reaction device in accordance with an exemplary embodiment.

FIG. 2 is a perspective view of a fluid analysis cartridge (reaction device) in accordance with an exemplary embodiment. Referring to FIG. 2, a fluid analysis cartridge (reaction device) 100 may include a housing 110 configured to support the fluid analysis cartridge 100 and a test device 120 within which a biochemical reaction between a fluid and a reagent occurs.

A grip portion 112 by which a user may hold the fluid analysis cartridge 100, and a fluid reservoir 111 in which a fluid may be contained may be disposed on the housing 110. The fluid reservoir 111 may include a hole 111a into which the fluid flows and a supply assistance unit 111b having a slanted surface so that the fluid easily flows into the hole 111a. A filter configured to remove blood corpuscles may be provided in the hole 111a. A plurality of chambers 121 may be provided on the test device 120 and configured to receive fluid from the fluid reservoir 111.

The chambers 121 provided on the test device 120 may include a reaction chamber in which a reagent for detecting various kinds of specimens is contained, and a control chamber in which the reagent for detecting the specimens is not contained.

Figure 3:
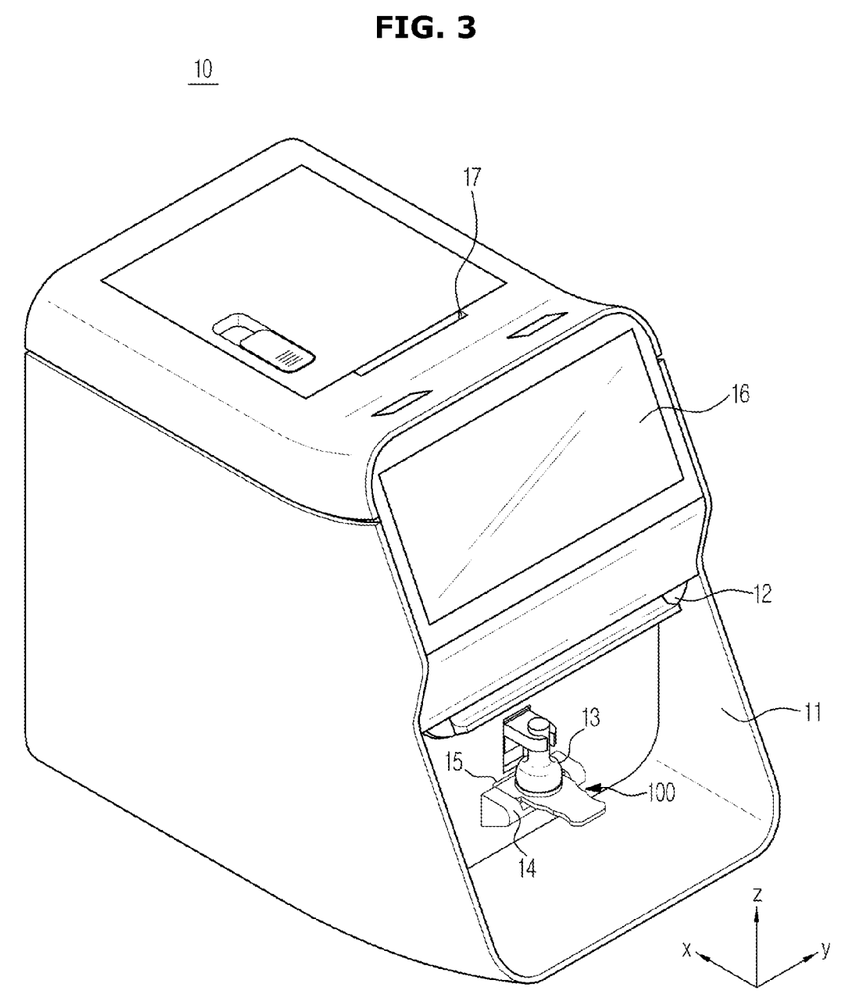
FIGS. 3 through 5 are schematic perspective views illustrating an outer appearance and operation of a test apparatus in accordance with an exemplary embodiment.

As shown in FIG. 3, the fluid analysis cartridge 100 may be inserted into the test apparatus 10.

While the kind of fluid sample serving as a test target is not limited to those described in the exemplary embodiments, for ease of explanation, it will be assumed in the present exemplary embodiment that the fluid sample is blood, the target material is an enzyme, the substrate that specifically reacts with the enzyme is a capture material, and the concentration of the enzyme is detected.

The test apparatus 10 may precisely detect the concentration of a target material present even in a small amount of blood using an automated test process.

Figure 4:
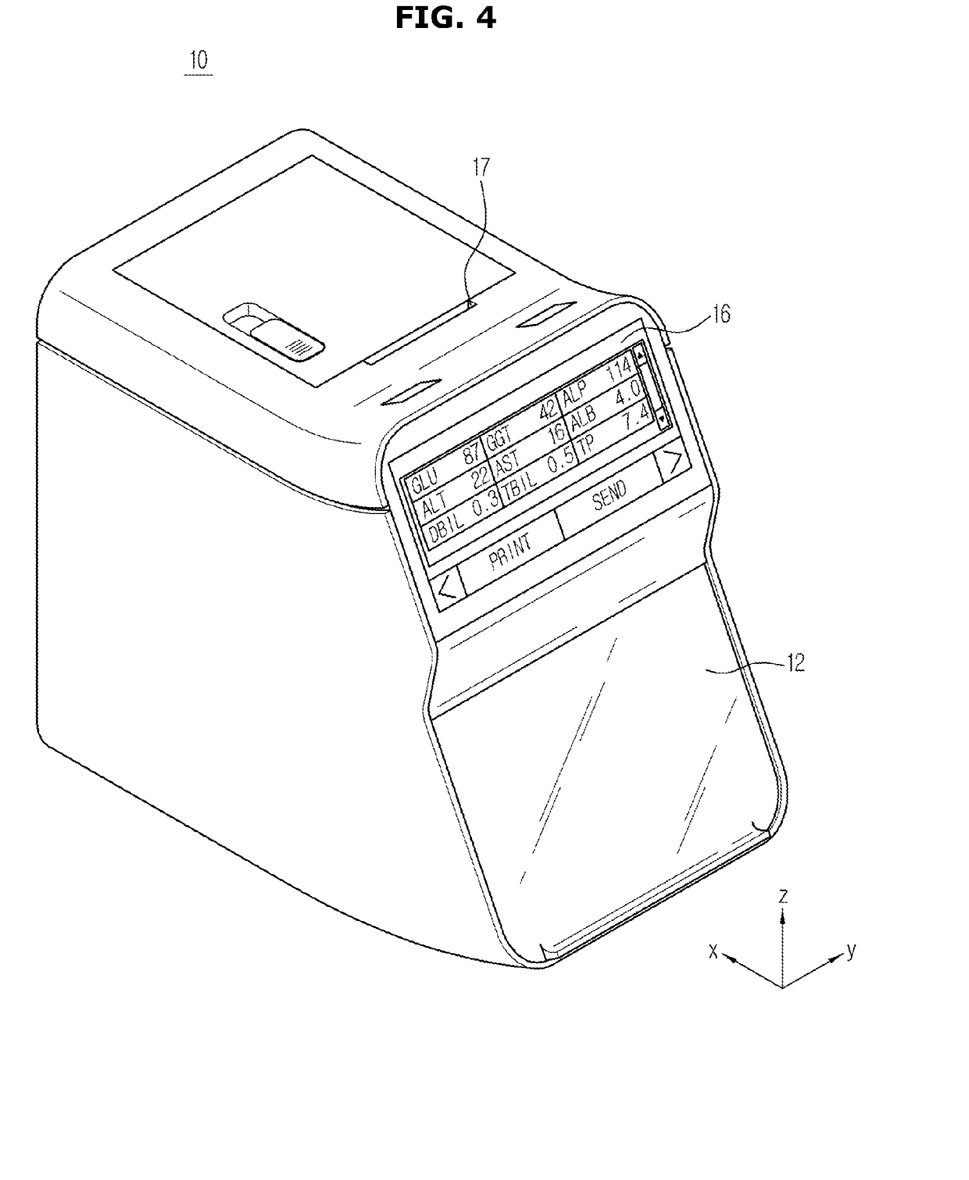
Figure 5:
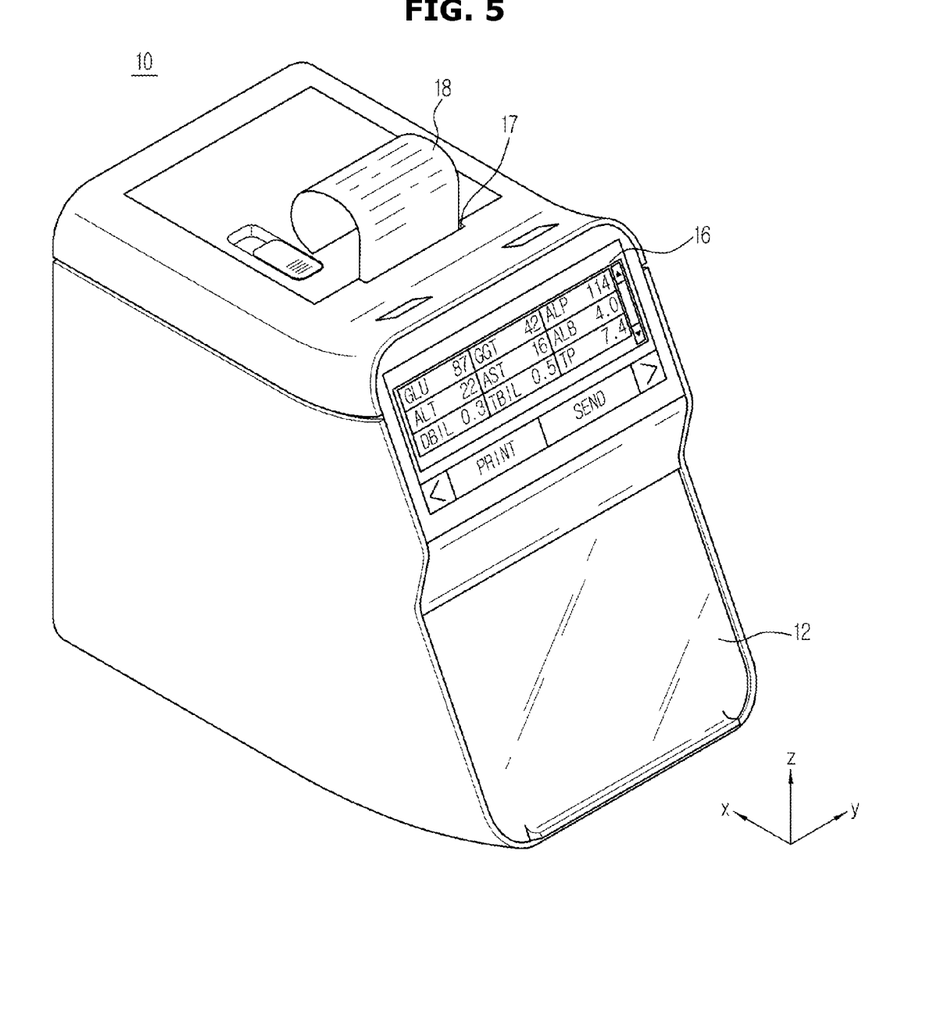

FIGS. 3 through 5 are schematic perspective views illustrating an outer appearance and operations of a test apparatus in accordance with an exemplary embodiment. Referring to FIG. 3, the test apparatus 10 may include a mounting unit 11 within which the fluid analysis cartridge 100 is mounted, a display 16 configured to display results obtained by testing the fluid analysis cartridge 100, and an output unit 17 configured to output the test results to printed matter.

When a door 12 of the mounting unit 11 slides upward and opens, the mounting unit 11 may be exposed. The fluid analysis cartridge 100 may then be inserted into an insertion slot 15 within the mounting unit 11, which may be configured so that the test device 120 of the fluid analysis cartridge 100 can be inserted into the test apparatus 10.

As described above, the test device 120 of the fluid analysis cartridge 100 may be inserted into the test apparatus 10, and the housing 110 may be exposed outside the test apparatus 10 while being supported by a housing support 14. When a pressure applicator 13 applies pressure to the fluid reservoir 111, the blood contained in the fluid reservoir 111 flows into the test device 120.

Figure 6A:
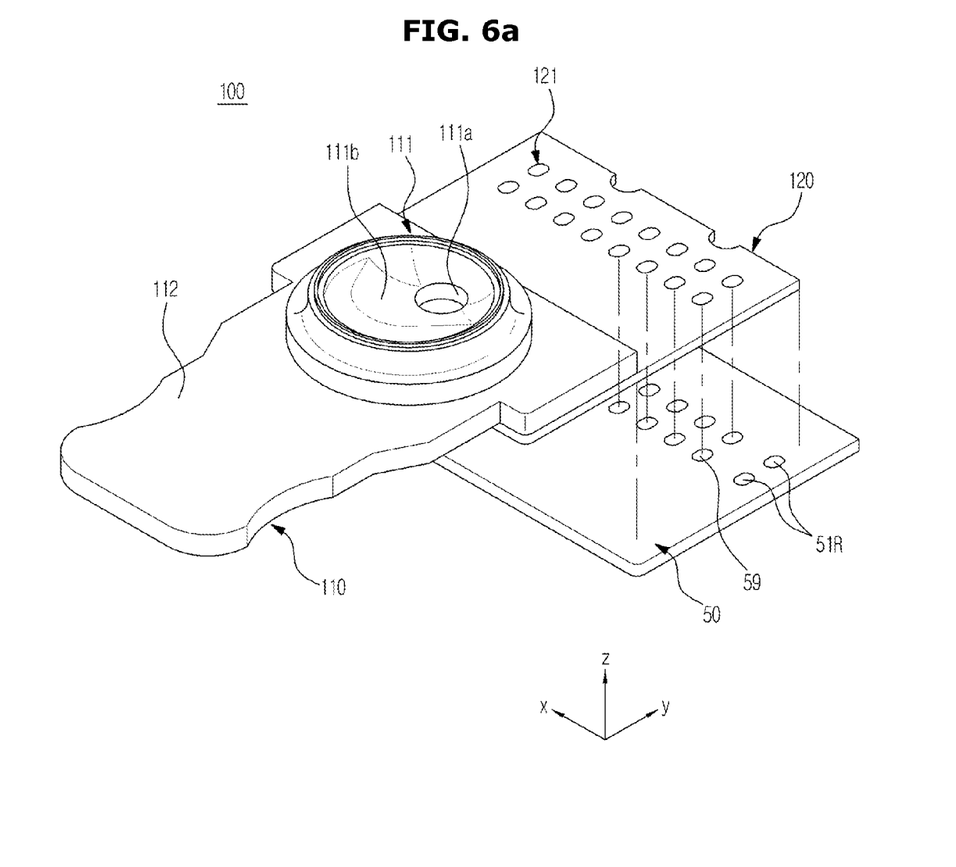
FIGS. 6A and 6B illustrate a relationship between a reaction device and a support.
Figure 6B:
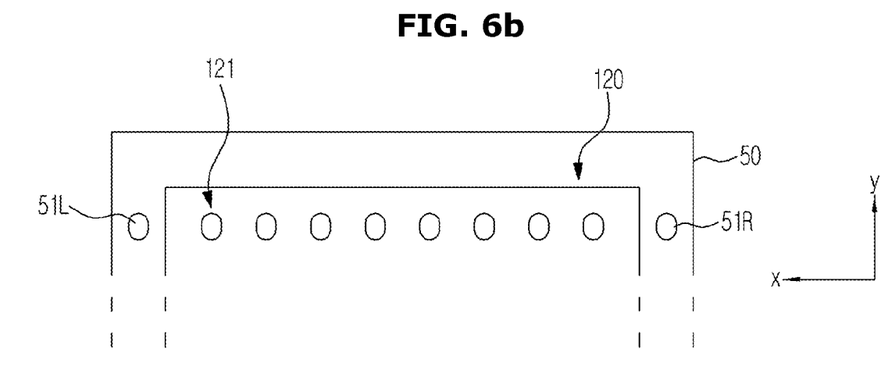

The test device 120 of the fluid analysis cartridge 100 may be supported by the support 50 for insertion into the test apparatus 10. Hereinafter, the support 50 will be described with reference to FIGS. 6A and 6B. As shown in FIGS. 6A and 6B, a plurality of holes 59 may be formed in the support 50. As shown in FIG. 6A, the holes 59 formed in the support 50 may be formed in positions corresponding respectively to the chambers 121 formed in the test device 120 of the fluid analysis cartridge 100. The number of the holes 59 formed in the support 50 may be greater than or equal to the number of the chambers 121 of the fluid analysis cartridge 100, and the size of each of the holes 59 formed in the support 50 may be greater than or equal to the size of each of the chambers 121 of the fluid analysis cartridge 100.

To measure the concentration of a specimen detected as a result of a reaction that occurred in a chamber 121 of the fluid analysis cartridge 100, light may be irradiated by the emitter 41 of the detector 40 to the chamber 121, as will be described later. The hole 59 may therefore be disposed in a position within the support 50 corresponding to the chamber 121 so as not to hinder the light irradiated to the chamber 121. In various embodiments, a transparent member may be formed in the support 50 rather than the hole 59.

The emitter 41 may irradiate light for use in measuring light absorptivity of the contents of the chamber 121. Irradiated light may thus pass through the hole 59 of the support unit 50 and be incident to the chamber 121 of the fluid analysis cartridge 100.

FIGS. 6A and 6B are diagrams showing a combination relationship between a reaction device and a support. As shown in FIGS. 6A and 6B, the support 50 may have a greater area than the test device 120.

In addition, as shown in FIG. 6B, a first hole 51L and a second hole 51R, which do not correspond to any chambers 121 of the test device 120, may be further formed in a region outside of the area of the test device 120. As shown in FIG. 6B, positions of the first hole 51L and the second hole 51R may be determined such that the first hole 51L and the second hole 51R are disposed in alignment with a row of chambers 121 of the test device 120. Results obtained by detecting the first hole 51L and the second hole 51R may be used to determine a positional error in the detector 40 due to the failing of the motor 42, to be described later.

In general, in order to properly perform a biochemical reaction, temperature conditions of the space in which the biochemical reaction occurs may be important. When appropriate temperature conditions are not satisfied, a reactant may be denatured, or the reaction may not occur properly. As a result, a desired material may not be detected. Accordingly, optimal temperature conditions for performing the reaction should be maintained until the reaction is completed. The support 50 may therefore include a component configured to maintain the test device 120 at a specific temperature as needed.

After inserting the fluid analysis cartridge 100 into the test apparatus 10, the door 12 may be closed, as shown in FIG. 4, and a test in the reaction device 100 may begin.

The test apparatus 10 may include the detector 40 including the emitter 41 and the light receiver 43.

The emitter 41 of the detector 40 may be embodied by a light source having a large emission area and capable of irradiating uniform light so that light can be directed to a predetermined region of the fluid analysis cartridge 100. For example, a backlight unit (BLU) may be used as the emitter 41. Alternatively, the emitter 41 may be a light source configured to be turned on and off at a predetermined frequency and embodied by a semiconductor emission device, such as a light emitting diode (LED) or a laser diode (LD), or a gas discharge lamp, such as a halogen lamp or a xenon (Xe) lamp.

The light receiver 43 of the detector 40 may be configured to detect light, which may be irradiated by the emitter 41 and transmitted through or reflected by a sample contained in a reaction chamber of the fluid analysis cartridge 100. The light receiver 43 may further be configured to generate an electric signal relative to the intensity of light. The light receiving unit 43 may include a depletion layer photodiode (PD), an avalanche PD, or a photomultiplier tube. Alternatively, the light receiving unit 43 may be embodied by a complementary metal oxide semiconductor (CMOS) image sensor or a charge-coupled device (CCD) image sensor.

The emitter 41 and the light receiver 43 may be positioned opposite each other with the reaction device 100 being disposed there between. In certain embodiments, the emitter 41 and the light receiver 43 may be positioned together above or under the reaction device 100.

The intensity or wavelength of light irradiated by the emitter 41 may be controlled in response to a command from the controller 30. The light receiving unit 43 may detect light and transmit a generated electric signal to the controller 30. The detector 40 may further include an analog-to-digital converter (ADC) configured to convert a detection result of the light receiver 43 into a digital signal, and output the digital signal to the controller 30.

When a blood sample moves from the fluid reservoir 111 of the fluid analysis cartridge 100 to the reaction chamber 121 containing a reagent for detecting a specimen, the detector 40 may irradiate light to the reaction chamber 121 under the control of the controller 30, detect light transmitted through the reaction chamber 121, and transmit a detection result to the controller 30. The controller 30 may further be configured to calculate light absorptivity based on the transmitted detection result, and detect the presence or absence of the specimen and/or the concentration of the specimen.

When a test is finished, as shown in FIG. 4, the display 16 of the test apparatus 10 may display a test result. Since the fluid analysis cartridge 100 may include a plurality of chambers 121, as shown in FIG. 2, a plurality of specimens may be detected from one fluid analysis cartridge 100. As shown in FIG. 4, when the plurality of specimens are detected, the display 16 may display test results regarding the plurality of specimens. Also, as shown in FIG. 5, the test results may be printed to paper 18 through the output unit 17.

The configuration of the test apparatus 10 shown in FIGS. 3 through 5 is only exemplary, and shapes and/or configurations of the test apparatus 10 may vary.

Figure 7:
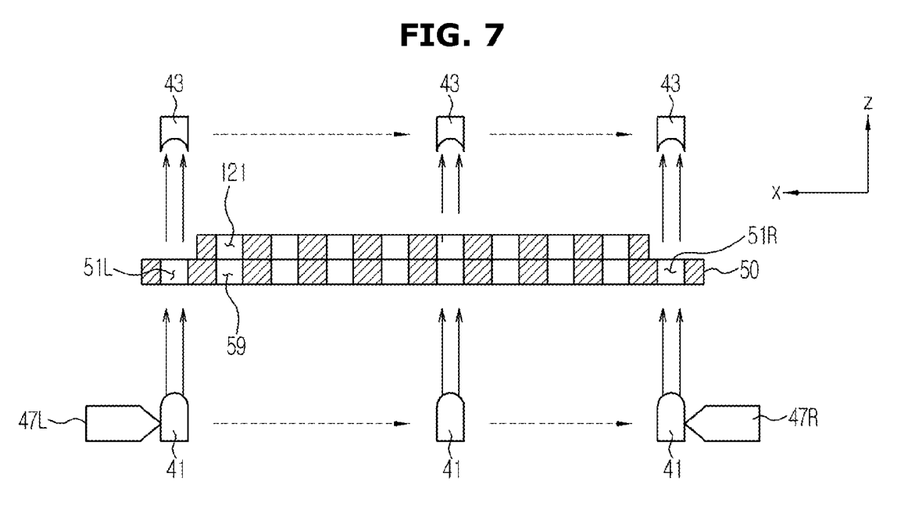
FIG. 7 illustrates a process of, by a detector in accordance with one embodiment of the present invention, radiating light onto a reaction device mounted on a support unit and detecting a detection target of in a chamber thereof, in accordance with an exemplary embodiment.

FIG. 7 is a cross-sectional view of the support 50 and the test device 120 of the fluid analysis cartridge 100. As shown in FIG. 7, the emitter 41 may irradiate light from below the support 50, and the light receiver 43 may receive light passing through the chamber 121 of the test device 120.

Thus a detector 40 may irradiate light to the chamber 121 of the test device 120 and measure light absorptivity while moving from the first hole 51L of the support 50 to the final second hole 51R.

The positional sensor 47 configured to sense whether the detector 40 is located in a reference position may be disposed below the support 50. As shown in FIG. 7, a first positional sensor 47L and a second positional sensor 47R may be respectively disposed in alignment with the first hole 51L and the second hole 51R of the support 50. Although FIG. 7 illustrates the first positional sensor 47L and the second positional sensor 47R, the support 50 may be provided with a single reference position corresponding to the first hole 51L with the second hole 51R being omitted.

The positional sensor 47 may be configured to output a sense signal to the controller 30 when the positional sensor 47 is in contact with the detector 40 or the detector 40 comes close to the positional sensor 47. Also, the positional sensor 47 may function to prevent the detector 40 from deviating from a reference position. That is, any deviation of the detector 40 from the reference position may be physically prevented by the positional sensor 47.

The motor 42 may be configured to move the detector 40. Referring to FIG. 7, the detector 40 may move from left to right (hereinafter, referred to as a first direction) and from right to left (hereinafter, referred to as a second direction) due to the motor 42. In various embodiments, a step motor may be used as the motor 42.

Since the motor 42 (esp., the step motor) rotates by as much as a predetermined angle according to a pulse input, an input value may also be a positional value. Thus, a positional error may occur when the step motor fails during the driving of the step motor because the step motor cannot rotate by as much as the predetermined angle. When such a positional error occurs in the detector 40, the detector 40 cannot detect a detection target in a precise position. Thus, the present exemplary embodiment provides a method of detecting and correcting a positional error due to the failing of the motor 42.

Figure 8:
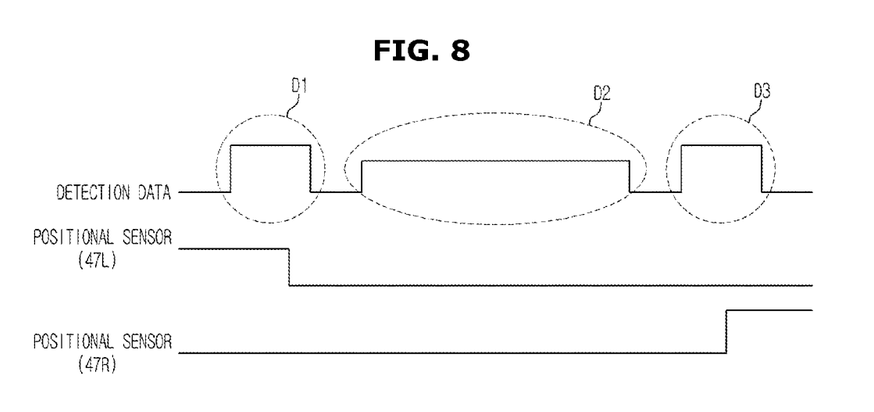
FIG. 8 is a graph showing detection data of a detector and sensing results of a positional sensor.
Figure 9:
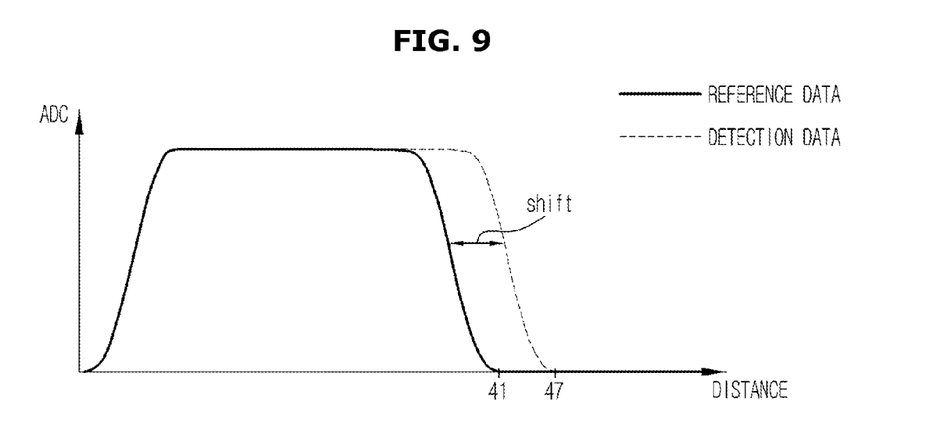
FIG. 9 is a graph showing a comparison between detection data of a detector and reference data.

FIG. 8 is a graph showing detection data of the detector 40 and sensing results of the positional sensor 47. FIG. 9 is a graph showing a comparison between detection data of the detector 40 and reference data.

The detection data shown in FIG. 8 has a waveform obtained by digitally converting light absorptivity of the chamber 121 of the test device 120, which was measured by the detector 40 while moving from the first hole 51L to the second hole 51R=.

Since the first hole 51L and the second hole 51R of the support 50 do not correspond to the chamber 121 of the test device 120, light transmitted through the first and second holes 51L and 51R always has the highest intensity. Accordingly, as shown in FIG. 8, it can be seen that data D1 corresponding to a detection result of the first hole 51L and data D3 corresponding to a detection result of the second hole 51R have a greater magnitude than data D2, which corresponds to a detection result of the chamber 121 disposed midway between the first and second holes 51L and 51R.

Data disposed in a middle region may therefore indicate detection results regarding a plurality of chambers 121 of the test device 120 of the fluid analysis cartridge 100. The intensity of light incident to the light receiver 43 through each of the chambers 121 may vary in accordance with the reaction performed in each of the corresponding chambers 121. Accordingly, pieces of data corresponding to each of the chambers 121 may have different magnitudes. Although the data is illustrated in a single waveform for brevity, waveforms having different magnitudes corresponding to the number of the chambers 121 may be actually obtained.

In various embodiments, the detector 40 begins by being positioned in alignment with the first hole 51L or the second hole 51R, and is sensed by the first positional sensor 47L or the second positional sensor 47R to output a signal. Thus, as shown in FIG. 8, data output by the first positional sensor 47L may rise to a high level in a position similar to the data D1 of the detection data of the detector 40, while data output by the second positional sensor 47R may rise to a high level in a position similar to the data D3 of the detection data of the detector 40. As shown in FIG. 8, a falling edge of the data output by the first positional sensor 47L may lead a falling edge of the data D1, and a rising edge of the data output by the second positional sensor 47R may trail a rising edge of the data D3. This is because the positional sensor 47 may sense the detector after the detector 40 measures light absorptivities of the first and second holes 51L and 51R due to the position in which the positional sensor 47 is disposed. However, the position of the positional sensor 47 is not limited to the above-described position, and relative positions of output data of the positional sensor 47 and detection data of the detector 40 as shown in FIG. 8 may vary.

The controller 30 may be configured to compare detection data of the detector 40 regarding the fluid analysis cartridge 100 with predetermined reference data, and determine whether there is a positional error in the detector 40.

The reference data may be data obtained by detecting the fluid analysis cartridge 100 using the detector 40 when the motor 42 does not fail. The reference data may include at least data obtained by detecting the first hole 51L and the second hole 51R of the support 50, that is, data corresponding to data D1 and D3 of the detection data shown in FIG. 8. The reference data may be preset and stored in a memory.

When the fluid analysis cartridge 100 is inserted into the test apparatus 10 and the test device 120 is supported by the support 50, the controller 30 may drive the motor 42 to move the detector 40 in a first direction.

In addition, the controller 30 may be configured to control the emitter 41 so that the detector 40 can irradiate light to each of the plurality of chambers 121 of the fluid analysis cartridge 100, and detect a detection target during the motion of the detector 40.

When the detector 40 is sensed by the second positional sensor 47R, the controller 30 may compare detection data of the detector 40 with reference data to determine whether a positional error in the detector 40 occurred while moving the detector 40 in the first direction. For example, the controller 30 may compare data D1 of the detection data shown in FIG. 8 with data (i.e., data regarding the first hole 51L) of the reference data, and determine an extent to which the detection data is shifted from the reference data.

FIG. 9 illustrates an extent to which detection data is shifted from reference data. Referring to FIG. 9, it can be seen that the detection data is shifted from the reference data by as much as 6 mm in the first direction. As discussed above, the controller 30 may be configured to compare the detection data with the reference data, determine the extent of the shift of the detector 40, and determine a positional error in the detector 40 based on the extent of shift.

Since a positional error in the detection data of the detector 40 has also occurred due to the positional error in the detector 40, the controller 30 may be configured to shift the detection data back by as much as the determined positional error and correct the detection data.

In addition, the controller 30 may be configured to control the driving of the motor 42, shift a position of the detector 40 back by as much as the determined positional error, and correct the positional error in the detector 40.

When the detector 40 reaches the second positional sensor 47R and finishes detecting the chamber 121 of the test device 120, the controller 30 may control the driving of the motor 42 to move the detector 40 in a second direction, which is the reverse direction of the first direction. Since the motor 42 may fail during motion of the detector 40 in the second direction, the controller 30 may repeat the above-described process of detecting and correcting the positional errors.

That is, the controller 30 may be configured to control the emitter 41 so that the detector 40 can irradiate light to each of a plurality of chambers 121 of the fluid analysis cartridge 100, and detect a detection target while moving in the second direction. When the first positional sensor 47L disposed at the end of the second direction sensed the detector 40, the controller 30 may compare detection data of the detector 40 during motion of the detector 40 in the second direction, with reference data, and determine whether a positional error occurred in the detector 40. Since a result of detection of each of the chambers 121 has been obtained during the motion of the detector 40 in the first direction, when the detector 40 moves in the second direction, detection of the plurality of chambers 121, except detection of the first hole 51L or the second hole 51R, may be omitted. To determine whether a positional error occurred, detection of the first hole 51L or the second hole 51R may be performed. When a positional error in the detector 40 is determined, the controller 30 may shift the detection data back by as much as the determined positional error and correct the detection data. Also, the controller 30 may be configured to shift a position of the detector 40 back by as much as the determined positional error and correct the positional error in the detector 40.

The above-described process of determining and correcting the positional error may vary.

As discussed above, the second positional sensor 47R may be omitted, while maintaining the ability to detect and correct any positional errors in the detector 40. For example, the controller 30 may be configured to move the detector 40 in the first direction to enable detection of the chambers 121. When the detection of the chambers 121 is completed, the controller 30 may be configured to move the detector 40 to an original position in the second direction. When the first positional sensor 47L senses the detector 40, the controller 30 may compare each piece of detection data with reference data, determine positional errors in the detector 40 caused during the motion of the detector 40 in the first and second directions, and correct positional errors in the detection data and the detector 40.

Alternatively, in addition to data regarding the first hole 51L and the second hole 51R, the controller 30 may be configured to compare detection data regarding the chambers 121 with reference data and determine any positional errors in the detector 40.

Figure 10:
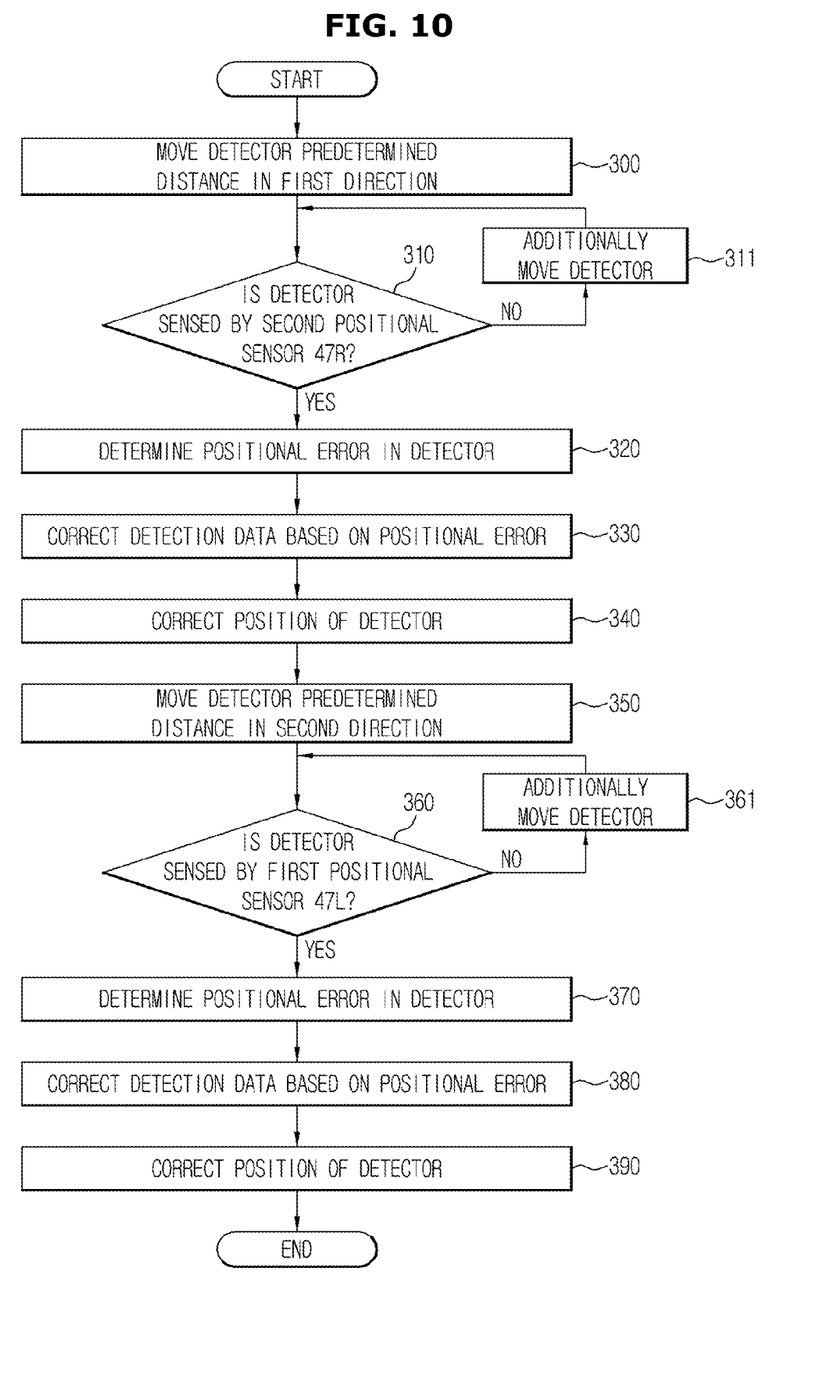
FIG. 10 is a flowchart illustrating a method of controlling a test apparatus in accordance with an exemplary embodiment.

FIG. 10 is a flowchart illustrating a method of controlling a test apparatus 10 in accordance with an exemplary embodiment.

As shown in FIG. 10, a controller 30 may be configured to move a detector 40 in a first direction (operation 300).

When a fluid analysis cartridge 100 is inserted into the test apparatus 10, the controller 30 may drive a motor 42 and move the detector 40 a predetermined distance in a first direction. For example, the controller 30 may be configured to move the detector 40 to a position corresponding to a second hole 51R. Also, the controller 30 may be configured to control an emitter 41 so that the detector 40 can irradiate light to each of a plurality of chambers 121 of the fluid analysis cartridge 100 and detect a detection target during motion.

When the detector 40 is sensed by a second positional sensor 47R (operation 310), the controller 30 may determine whether a positional error in the detector 40 occurred (operation 320). When the detector 40 is not sensed by the second positional sensor 47R, the detector 40 may be moved further in the first direction (operation 311). When the detector 40 is sensed by the second positional sensor 47R disposed at the end of the first direction, the controller 30 may compare detection data of the detector 40 with reference data and determine any positional errors in the detector 40 while moving the detector 40 in the first direction.

For instance, the controller 30 may be configured to compare data D1 of the detection data shown in FIG. 8 with data corresponding to data (i.e., data regarding a first hole 51L) of the reference data corresponding to the data D1, and determine an extent by which the detection data is shifted from the reference data.

FIG. 9 illustrates an example of the extent by which detection data is shifted from reference data. Referring to FIG. 9, it can be seen that the detection data is shifted from the reference data by as much as 6 mm in the first direction. Thus, the controller 30 may be configured to compare the detection data with the reference data, determine a shifted extent of the detector 40, and determine a positional error in the detector 40 based on the shifted extent.

Although a time point during which the positional error in the detector 40 is determined may be a time point during which the detector 40 is sensed by the second positional sensor 47R, as described above, the exemplary embodiments described herein are not limited thereto. That is, when the detector 40 is moved a predetermined distance, data of the detector 40 may be compared with reference data, and the positional error in the detector 40 may be determined. For instance, when the detector 40 is moved in the first direction and reaches the second hole 51R, the detection data of the detector 40 may be compared with the reference data to determine the positional error in the detector 40. It may be confirmed via a rotational angle or steps of the motor 42 whether the detector 40 has been moved the predetermined distance.

After the positional error in the detector 40 is determined, the controller 30 may correct the detection data based on the positional error (operation 330), and correct a position of the detector 40 (operation 340).

Since a positional error in the detection data of the detector 40 also occurs due to a positional error in the detector 40, the controller 30 may be configured to reversely shift the detection data back by as much as the determined positional error and correct the detection data. Also, the controller 30 may be configured to control the driving of the motor 42, reversely shift a position of the detector 40 back by as much as the determined positional error, and correct the positional error in the detector 40.

The above-described process of determining and correcting positional errors may vary. As discussed above, the second positional sensor 47R may be omitted, and the positional error in the detector 40 may still be detected and corrected. For example, the controller 30 may be configured to move the detector 40 in the first direction to enable detection of the chamber 121. When the detection of the chamber 121 is completed, the controller 30 may move the detector 40 to an original position in a second direction to enable detection of the chamber 121. When the detector 40 is sensed by the first positional sensor 47L, the controller 30 may then compare each piece of detection data with reference data, determine positional errors in the detector 40 caused during the motion of the detector 40 in the first and second directions, and correct positional errors in the detection data and the detector 40.

Alternatively, in addition to data regarding the first hole 51L and the second hole 51R, the controller 30 may be configured to compare detection data regarding the chamber 121 with reference data and determine a positional error in the detector 40.

Thus, the controller 30 may be configured to move the detector 40 a predetermined distance in the second direction (operation 350). When the controller 30 is sensed by the first positional sensor 47L (operation 360), the controller 30 may determine whether a positional error occurred in the detector 40 (operation 370). When the detector 40 is not sensed by the first positional sensor 47L, the controller 30 may move the detector 40 further in the second direction (operation 361).

When the detector 40 reaches the second positional sensor 47R and finishes detecting the chamber 121 of the test device 120, the controller 30 may control the driving of the motor 42 and move the detector 40 in the second direction, which is the opposite direction to the first direction. Since the motor 42 may fail during motion of the detector 40 in the second direction, the controller 30 may be configured to repeat the above-described process of detecting and correcting the positional errors.

That is, the controller 30 may be configured to control the emitter 41 so that the detector 40 can irradiate light to each of a plurality of chambers 121 of the fluid analysis cartridge 100 and detect a detection target while moving in the second direction. When the detector 40 is sensed by the first positional sensor 47L disposed at the end of the second direction, the controller 30 may compare detection data of the detector 40 during the motion of the detector 40 in the second direction, with reference data, and determine whether a positional error occurred in the detector 40. Since a result of detection of each of the chambers 121 has been obtained during the motion of the detector 40 in the first direction, when the detector 40 moves in the second direction, detection of the plurality of chambers 121 may be omitted, except detection of the first hole 51L or the second hole 51R. To determine a positional error, detection of the first hole 51L or the second hole 51R may be performed. As described above, a time point in which the positional error in the detector 40 is determined is not limited to a time point in which the detector 40 is sensed by the first positional sensor 47L. When the detector 40 moves a predetermined distance, data of the detector 40 may be compared with reference data, and a positional error in the detector 40 may be determined. For example, when the detector 40 moves in the second direction and reaches the first hole 51L, detection data of the detector 40 may be compared with reference data, and a positional error in the detector 40 may be determined. It may be confirmed via a rotational angle of the motor 42 or steps whether the detector 40 has been moved a predetermined distance.

When a positional error in the detector 40 is determined to exist, the controller 30 may correct the detection data based on the positional error (operation 380), and correct the position of the detector 40 (operation 390).

When the positional error in the detector 40 is determined, the controller 30 may shift the detection data back by as much as the determined positional error and correct the detection data since a positional error in the detection data of the detector 40 has also occurred due to the positional error in the detector 40. Also, the controller 30 may be configured to control the driving of the motor 42, shift a position of the detector 40 back by as much as the determined positional error, and correct the positional error in the detector 40.

In an exemplary embodiment, positional errors in the detector 40 and data due to the failing of the motor 42 may be detected and corrected without additional mechanical hardware or circuitry.

Although a few exemplary embodiments of the present invention have been shown and described, it would be appreciated by those skilled in the art that changes may be made in these embodiments without departing from the principles and spirit of the inventive concept, the scope of which is defined in the claims and their equivalents.

What is claimed is:

1. A test apparatus comprising:
   a detector configured to irradiate light to a plurality of chambers of a reaction device and detect a detection target; a motor connected to the detector to move the detector such that light is irradiated to the plurality of chambers; and a controller configured to compare detection data received from the detector regarding the reaction device with reference data, determine a positional error in the lateral movement of the detector, and correct the lateral positional error.

2. The apparatus according to claim 1, further comprising:
   a support configured to support the reaction device inserted into the test apparatus, the support including first and second holes formed adjacent to and at opposite sides of the reaction device; and
   at least one positional sensor disposed adjacent to the first and second holes and under the support, and configured to sense the detector when the detector moves to a position corresponding to one of the holes.

3. The apparatus according to claim 2, wherein the controller is configured to compare the detection data of the detector regarding at least one of the first and second holes with reference data, determine an extent by which the detection data of the detector is shifted from the reference data, and determine the positional error in the detector based on the extent of the shifted data.

4. The apparatus according to claim 3, wherein the controller is configured to shift the detection data regarding the plurality of chambers back by as much as the determined positional error, and correct the detection data.

5. The apparatus according to claim 3, wherein the controller is configured to drive the motor to move the detector back by as much as the positional error, thereby correcting the positional error in the detector.

6. The apparatus according to claim 1, wherein the controller is configured to compare the detection data of the detector regarding any one of the plurality of chambers with reference data corresponding to the detection data, determine an extent by which the detection data of the detector is shifted from the reference data, and determine the positional error in the detector based on the extent of the shifted data.

7. The apparatus according to claim 1, wherein the controller is configured to compare the detection data of the detector with the predetermined reference data, determine the positional error in the detector, and correct the positional error while the detector is moving.

8. The apparatus according to claim 2, wherein the controller is configured to drive the motor, move the detector in a first direction, and control the detector so that the detector irradiates light to each of the plurality of chambers of the reaction device and detects a detection target while moving, and
   the controller is configured to compare detection data of the detector regarding at least one of the two holes with reference data regarding the corresponding hole, determine an extent to which the detection data of the detector is shifted from the reference data, and determine the positional error in the detector based on the extent of the shifted data in response to the detector moving a predetermined distance.

9. The apparatus according to claim 2, wherein the controller is configured to compare the detection data of the detector with predetermined reference data, determine the positional error in the detector, and correct the positional error in the detector in response to the detector being sensed by the at least one positional sensor.

10. A method of controlling a test apparatus,
comprising: driving a motor configured to move a detector which is connected to the motor in a first direction; comparing detection data regarding a plurality of chambers of a reaction device while the detector is moving, with reference data and determining a positional error in the lateral movement of the detector; and correcting the lateral positional error.

11. The method according to claim 10, further comprising:
comparing detection data of the detector regarding any one of the plurality of chambers of the reaction device with reference data corresponding to the detection data, and determining an extent by which the detection data of the detector is shifted from the reference data; and
determining the positional error in the detector based on the determined extent of shift.

12. The method according to claim 10, wherein the correcting of the positional error comprises shifting the detection data of the detector back by as much as the determined positional error and correcting the detection data.

13. The method according to claim 10, wherein the correcting of the positional error comprises driving the motor to move the detector back by as much as the positional error to correct the positional error in the detector.

14. The method according to claim 10, wherein the test apparatus comprises:
a support configured to support the reaction device inserted therein, the support including two holes formed adjacent to and at opposite sides of a position in which the reaction device is located; and
at least one positional sensor disposed adjacent to and under the support and configured to sense the detector when the detector moves to a position corresponding to one of the holes.

15. The method according to claim 14, wherein the determining of the positional error comprises:
comparing the detection data of the detector regarding at least one of the two holes with reference data regarding the corresponding hole;
determining an extent by which the detection data of the detector is shifted from the reference data; and
determining the positional error in the detector based on the extent of the shift.

16. The method according to claim 14, further comprising:
controlling the detector so that the detector irradiates light to each of the plurality of chambers of the reaction device and detects a detection target while moving;
comparing detection data of the detector regarding at least one of the two holes with reference data regarding the corresponding hole and determining an extent by which the detection data of the detector is shifted from the reference data when the detector moves a predetermined distance; and
determining the positional error in the detector based on the determined extent of shift.

17. The method according to claim 14, further comprising:
controlling the detector so that the detector irradiates light to each of the plurality of chambers of the reaction device and detects a detection target while moving;
comparing detection data of the detector regarding at least one of the two holes with reference data regarding the corresponding hole and determining an extent by which the detection data of the detector is shifted from the reference data when a positional sensor located in the moving direction senses the detector; and
determining the positional error in the detector based on the determined extent of shift.

18. The apparatus according to claim 1, wherein the detector comprises a light source to irradiate the light to the plurality of chambers, and wherein the motor is connected to the light source to move the light source.

19. The apparatus according to claim 18, wherein the controller is configured to determine the positional error of the detector by comparing a displacement shift of a maximum value of the measured detection data and a maximum value of the reference data.

20. The apparatus according to claim 18, wherein the motor moves the light source in a linear direction over the plurality of chambers arranged in the linear direction.

* * * * *